United States Patent
Tsubooka

(10) Patent No.: US 10,207,083 B2
(45) Date of Patent: Feb. 19, 2019

(54) BALLOON CATHETER AND METHOD FOR MANUFACTURING BALLOON

(71) Applicant: TERUMO KABUSHIKI KAISHA, Shibuya-ku, Tokyo (JP)

(72) Inventor: Michiyo Tsubooka, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 405 days.

(21) Appl. No.: 15/201,973

(22) Filed: Jul. 5, 2016

(65) Prior Publication Data
US 2017/0007805 A1   Jan. 12, 2017

(30) Foreign Application Priority Data

Jul. 6, 2015 (JP) ................................. 2015-135565

(51) Int. Cl.
*A61M 25/10* (2013.01)
*A61B 17/3207* (2006.01)
(Continued)

(52) U.S. Cl.
CPC ......... *A61M 25/1002* (2013.01); *A61B 17/22* (2013.01); *A61B 17/320725* (2013.01);
(Continued)

(58) Field of Classification Search
CPC ............ A61M 25/1002; A61M 25/104; A61M 25/1029; A61M 2025/1004; A61M 2025/1031; A61M 2025/1086; A61M 25/1018; A61M 25/1011; A61M 25/1038; A61B 17/22; A61B 17/320725;
(Continued)

(56) References Cited

U.S. PATENT DOCUMENTS

2003/0144683 A1   7/2003 Sirhan et al.
2011/0160756 A1   6/2011 Aggerholm et al.
(Continued)

FOREIGN PATENT DOCUMENTS

JP   2009-112361 A   5/2009
WO   94/23787 A1   10/1994

OTHER PUBLICATIONS

Extended European Search Report dated Nov. 28, 2016 issued by the European Patent Office in corresponding European Patent Application No. 16175461.9 (6 pages).

*Primary Examiner* — Katrina Stransky
*Assistant Examiner* — Michael Mendoza
(74) *Attorney, Agent, or Firm* — Buchanan Ingersoll & Rooney PC

(57) ABSTRACT

A balloon catheter includes a flexible elongated shaft and a balloon fixed to the distal portion of the shaft. The balloon expands and contracts. The balloon includes an effective expansion portion and at least one projection portion on the effective expansion portion. The effective expansion portion possesses a cylindrical shape when the balloon is expanded, and the projection portion extends for a predetermined length along the axial direction of the balloon. The projection portion has first and second parts so that the inner surface of the first part of the balloon faces the inner surface of the second part of the balloon. The first and second parts project radially outwardly away from immediately adjacent parts of the balloon. The inner surface of the first part of the balloon is at least partially welded to the inner surface of the second part of the balloon.

20 Claims, 10 Drawing Sheets

(51) Int. Cl.
*A61B 17/22* (2006.01)
*A61B 17/00* (2006.01)

(52) U.S. Cl.
CPC ...... *A61M 25/104* (2013.01); *A61M 25/1029* (2013.01); *A61B 2017/00526* (2013.01); *A61B 2017/22001* (2013.01); *A61B 2017/22051* (2013.01); *A61M 2025/1004* (2013.01); *A61M 2025/1031* (2013.01); *A61M 2025/1086* (2013.01)

(58) Field of Classification Search
CPC ........... A61B 2017/22051; A61B 2017/00526; A61B 2017/22001
See application file for complete search history.

(56) References Cited

U.S. PATENT DOCUMENTS

| | | |
|---|---|---|
| 2012/0130407 A1 | 5/2012 | Aggerholm et al. |
| 2014/0088624 A1 | 3/2014 | Burton et al. |

BALLOON CATHETER AND METHOD FOR MANUFACTURING BALLOON

CROSS-REFERENCES TO RELATED APPLICATIONS

This application is a continuation of Japanese Application No. 2015-135565 filed on Jul. 6, 2015, the entire content of which is incorporated herein by reference.

TECHNICAL FIELD

The present invention relates to a balloon catheter which is a medical device, and a method for manufacturing the balloon provided in the balloon catheter.

BACKGROUND DISCUSSION

A balloon catheter has been widely known as a medical device which widens a stenosed site formed in a living body. In recent years, a blade (elongated member) formed of a resin or metal having comparatively high rigidity has been proposed for installation on the outer surface side of the balloon of a balloon catheter. For example, Japanese Patent Application No. JP-A-2009-112361 discloses one type of balloon catheter with a blade installed on the outer surface of the balloon.

The balloon catheter provided with a blade as described above makes it possible to have the blade bite into the stenosed site (i.e., cut into the stenosed site) when the balloon is expanded while treating the stenosed site, and to perform treatment in which the stenosed site is widened while being cut into the blade (e.g., so that portions of the stenosed site are removed). For this reason, it is possible to exhibit a high treatment effect even in, for example, treatment of a lesion area (arteriosclerosis site or the like) in which calcification proceeds, or the like (i.e., the treatment method with the balloon catheter can be effective even when treating a lesion site that includes calcification).

SUMMARY OF THE INVENTION

If a blade formed of a member different from a balloon (i.e., a different material) is installed on the balloon and has comparatively high rigidity (i.e., the blade is more rigid than the balloon), there is a possibility that the flexibility of the balloon may be impaired and the blade may be detached from the balloon. During the manufacturing of a balloon, it is necessary to perform a step of installing a blade on the balloon in addition to a step of preparing the blade (i.e., forming the blade). These steps increase the complexity of manufacturing and/or increase the manufacturing costs due to an increase in the number of parts.

Furthermore, there is a concern that the outer surface of the balloon may be damaged by the blade. When folding the balloon or when operating the balloon in a body lumen, there are increased chances for the blade to come into contact with the outer surface of the balloon (and potentially cut or rupture the balloon). Therefore, it is difficult to prevent the generation of such damage to the balloon.

The balloon catheter disclosed here can improve the performance of expanding the balloon and can prevent the occurrence of various problems caused by providing a blade formed of a member different from the balloon. The method for manufacturing a balloon disclosed here may also provide manufacturing benefits to produce a suitable balloon catheter.

The balloon catheter disclosed here includes a flexible elongated shaft and a balloon fixed to the distal portion of the shaft. The balloon expands and contracts. The balloon includes an effective expansion portion and at least one projection portion on the effective expansion portion. The effective expansion portion possesses a cylindrical shape when the balloon is expanded, and the projection portion extends for a predetermined length along the axial direction of the balloon. The projection portion has first and second parts so that the inner surface of the first part of the balloon faces the inner surface of the second part of the balloon. The first and second parts project radially outwardly away from immediately adjacent parts of the balloon. The inner surface of the first part of the balloon is at least partially welded to the inner surface of the second part of the balloon.

Another aspect of the disclosure here involves a balloon catheter which includes an elongated shaft which is flexible and a balloon fixed to the distal portion of the shaft. The balloon is configured to expand outward in a radial direction and contract inward in the radial direction. The balloon includes an effective expansion portion which is cylindrically shaped when the balloon is expanded and at least one projection portion protruding radially outward. The projection portion extends radially outward beyond the effective expansion portion when the balloon is expanded. The entire balloon is integrally formed in one piece at the same time such that the effective expansion portion and the projection portion of the balloon are a unitary structure.

According to the present invention, there is provided a method for manufacturing a balloon which includes: a balloon molding step of molding a tubular balloon material in a balloon having a predetermined shape; and a projection portion-forming step of making a part of the balloon protrude outward in a radial direction by at least partially welding the adjacent inner surfaces to each other in a portion in which the inner surfaces of the balloon are made to face each other, to form at least one projection portion having a predetermined length along an axial direction of the balloon.

The disclosed balloon catheter allows improved performance when expanding a balloon with respect to a stenosed site and using a projection portion formed on the outer surface of the balloon to engage the stenosed site. Since the projection portion is constituted by a part of the balloon (i.e., the balloon is a unitary structure that includes the projection portion), it is possible to prevent a decrease in flexibility of a balloon that is caused when a blade formed of a member different from the balloon is installed on the balloon. Utilizing a projection portion that constitutes part of the balloon itself also makes it possible to prevent other problems such as detachment of the blade from the balloon. The manufacturing of the balloon catheter here is simpler/easier and the number of parts can be reduced compared to the case where a blade is installed as a separate component. Therefore, it is possible to decrease manufacturing costs. Furthermore, the balloon and the projection portion are formed of the same material as each other, and it is thus possible to suitably prevent damage on the outer surface of the balloon during folding of the balloon or during operation of the balloon in a biological lumen.

BRIEF DESCRIPTION OF THE DRAWINGS

FIG. 1A is a perspective view showing an enlarged distal side of the balloon catheter, FIG. 1B is a cross-sectional view taken along line 1B-1B shown in FIG. 1A, and FIG. 1C is a view showing an enlarged portion which is identified by the dotted line 1C in FIG. 1B.

FIG. 2A is a view showing a simplified overall configuration of the balloon catheter and FIG. 2B is an enlarged cross-sectional view showing a cross section of the balloon catheter on the distal side.

FIG. 3A is a view showing a state when the balloon is molded, FIG. 3B is a partially enlarged view showing an inner surface-opposed portion formed in the balloon, and FIG. 3C is a partially enlarged view showing a state when a projection portion is formed on the balloon.

FIG. 4A is a view showing a state when the blade portion is formed on the balloon, FIG. 4B is a view showing a state when the balloon possessing the blade portion is folded, and FIG. 4C is a view showing a state when the folded balloon is inserted into a protection sheath.

FIG. 5A is a perspective view showing an enlarged distal side of the balloon catheter, FIG. 5B is a cross-sectional view taken along line 5B-5B shown in FIG. 5A, and FIG. 5C is a view showing an enlarged portion identified by the dotted line 5C in FIG. 5B.

FIG. 6A is a perspective view showing an enlarged distal side of the balloon catheter, FIG. 6B is a cross-sectional view taken along line 6B-6B shown in FIG. 6A, and FIG. 6C is a cross-sectional view taken along line 6C-6C shown in FIG. 6A.

FIG. 7A is a perspective view showing an enlarged distal side of the balloon catheter and FIG. 7B is a cross-sectional view taken along line 7B-7B shown in FIG. 7A.

FIG. 8A is a view showing a state when the balloon is molded and FIG. 8B is a view showing a state when a projection portion is formed on the molded balloon.

DESCRIPTION OF EMBODIMENTS

Figure 1A:
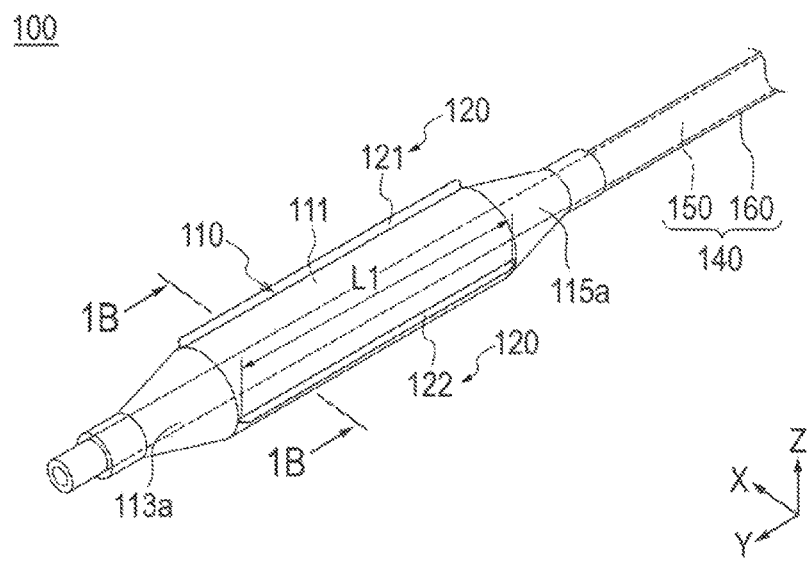
FIGS. 1A-1C are views showing a balloon catheter according to a first embodiment.

A balloon catheter and method of manufacturing a balloon catheter according to the described aspects of the present disclosure will be described in detail below, with reference to several embodiments illustrated in the attached drawings, which embodiments represent examples of the inventive balloon catheter and method of manufacturing the balloon catheter disclosed here. Note that the dimensional ratios in the drawings may be exaggerated and different from the actual ratios for the convenience of description.

In the description of the embodiments, the side (end) of the catheter on which the balloon is provided is called a distal side (end) or distal portion, the side (end) on which the hub is provided is called a proximal side (end) or proximal portion, and the direction in which the shaft extends is called an axial direction. An X-axis denoted on a drawing represents a width direction of the balloon catheter and a Y-axis represents the axial direction of the balloon catheter. In addition, a Z-axis represents a direction orthogonal to a plane formed by the X-axis and the Y-axis.

First Embodiment

Figure 3A:
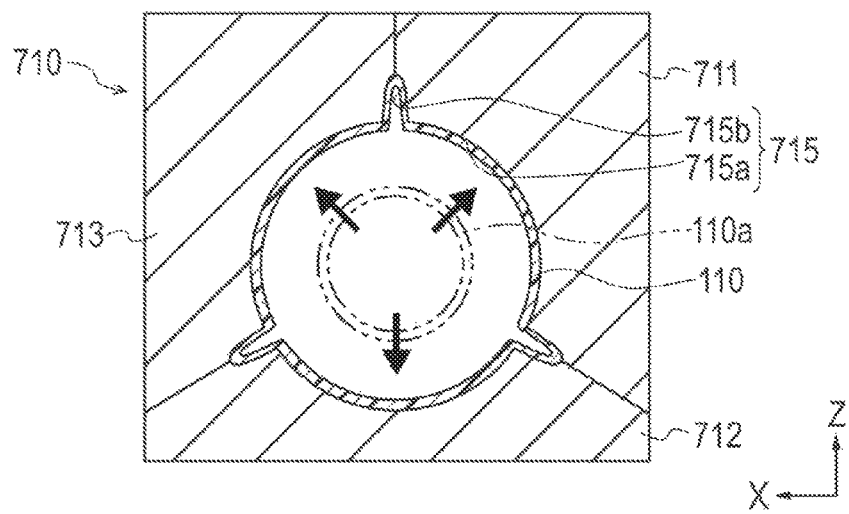
FIGS. 3A-3C are views for illustrating a manufacturing step of a balloon according to the first embodiment.
Figure 3B:
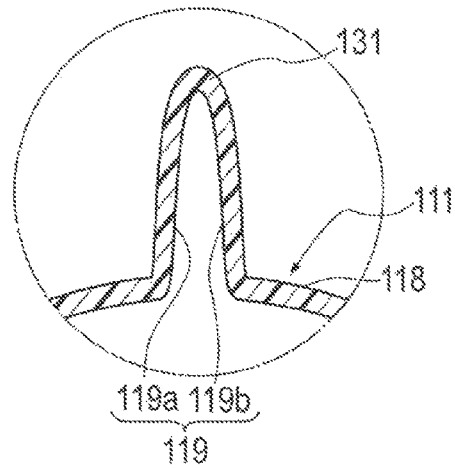
Figure 3C:
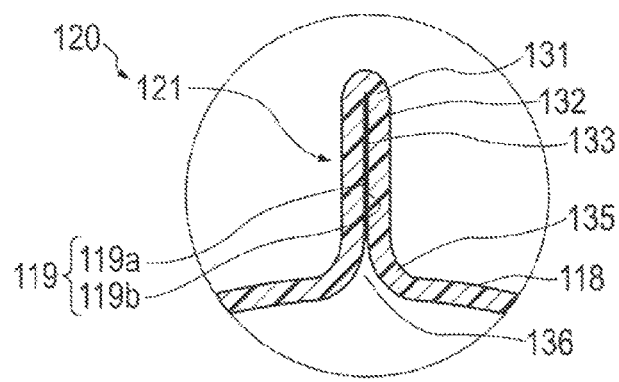
Figure 4A:
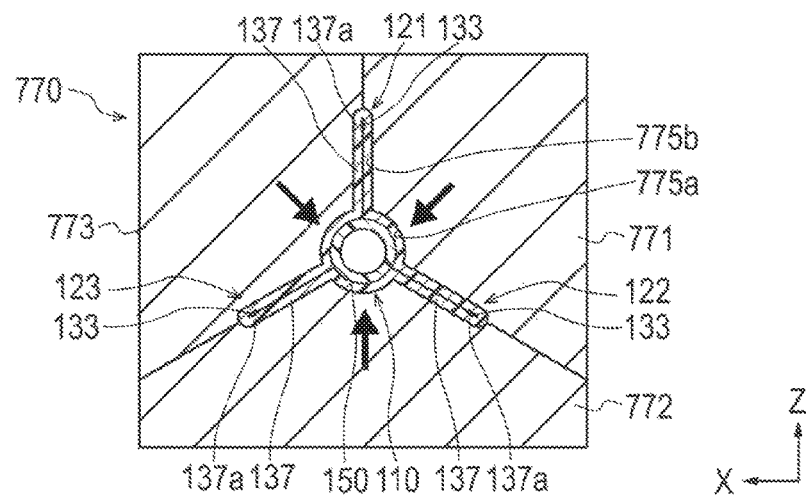
FIGS. 4A-4C are views for illustrating an operation step of forming a blade portion on a balloon.
Figure 4B:
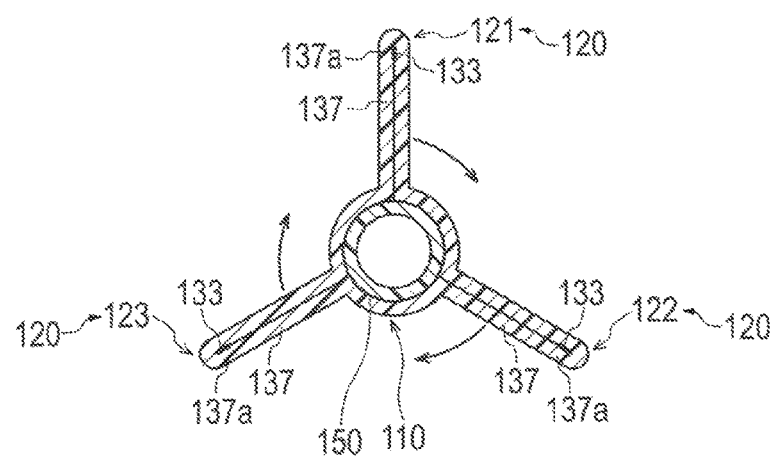
Figure 4C:
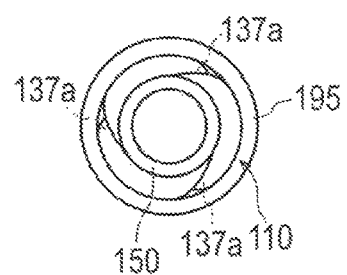

FIGS. 1A-2B show a configuration of each portion of a balloon catheter according to a first embodiment. FIGS. 3A-3C show the manufacturing of a balloon provided in the balloon catheter according to the first embodiment (i.e., the method of manufacturing the balloon of the balloon catheter illustrated in FIGS. 1A-2B). FIGS. 4A-4C illustrate an operation step of forming a blade portion on a balloon.

Figure 2A:
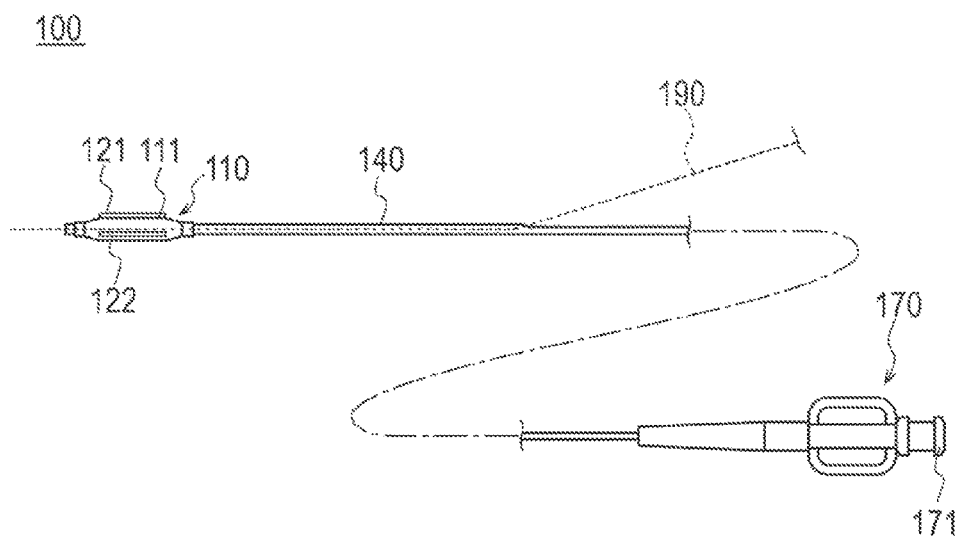
FIGS. 2A and 2B are views showing the balloon catheter according to the first embodiment.
Figure 2B:
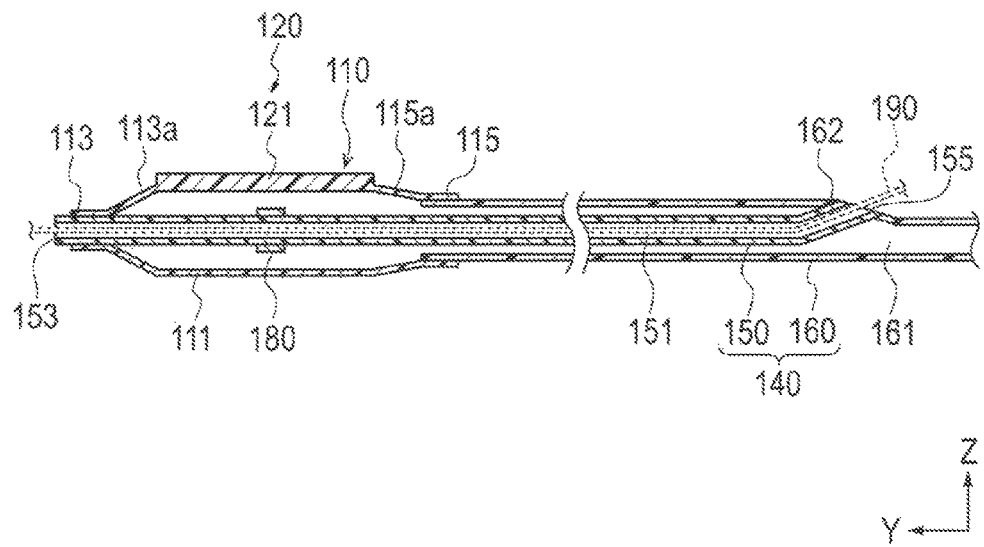

As illustrated in FIGS. 2A-2B, a balloon catheter 100 according to the present embodiment is a medical device which performs treatment (i.e., an operator uses to perform treatment) by inserting a shaft 140 into a biological organ (i.e., in a living body) and expanding (i.e., dilating or inflating) a balloon 110 disposed on a distal side of the shaft 140 in a stenosed site (lesion area) to widen the stenosed site.

The balloon catheter 100 is a balloon catheter for expansion in percutaneous transluminal coronary angioplasty ("PTCA") which is used for widening a stenosed site of the coronary artery. The balloon catheter 100 can also be used to treat and improve a stenosed site formed in, for example, other blood vessels, the bile duct, the trachea, the esophagus, other digestive tract, the urethra, lumens in the nose and the ears, and biological organs (e.g., other organs).

The configuration of each portion of the balloon catheter 100 will be described.

As shown in FIGS. 2A-2B, the balloon catheter 100 includes the elongated shaft 140 which can be inserted into a biological lumen and has flexibility. The balloon 110 is fixed to a distal portion of the shaft 140 and can be expanded and contracted. The balloon catheter 100 also includes a hub 170 which is disposed on a proximal portion side of the shaft 140.

The balloon catheter 100 is a so-called rapid exchange type balloon catheter provided with an opening portion 155 (i.e., a guide wire lumen) through which a guide wire 190 is movable to the distal portion side of the shaft 140. However, the balloon catheter 100 can also be a so-called over-the-wire type balloon catheter in which a guide wire lumen is formed within the balloon catheter 100, extending from a distal end of a shaft to a proximal end of the shaft.

As shown in FIG. 2B, the shaft 140 includes an inner tube (inner tube shaft) 150 in which a guide wire lumen 151 through which the guide wire 190 is inserted is formed, and an outer tube (outer tube shaft) 160 which forms a pressurization medium lumen 161 that enables a pressurization medium to flow between the inner tube 150 and the outer tube 160 (i.e., the space between the inner surface of the outer tube 160 and the outer surface of the inner tube 150 is the pressurization medium lumen 161).

The shaft 140 has a double-tube structure in which the inner tube 150 and the outer tube 160 are concentrically positioned, with the inner tube 150 being inserted into the outer tube 160 (i.e., the inner tube 150 extends within the interior of the outer tube 160).

The inner tube 150 is formed of a hollow tube material (i.e., a cylindrical or tubularly-shaped material) of which a proximal side is curved radially outward (i.e., the proximal end of the inner tube 150 bends towards the radially outward side). A distal portion 113 of the balloon 110 is liquid-tightly and airtightly bonded (i.e., bonded to be liquid and air tight such that liquid and air are prevented from being introduced into the interior of the balloon 110) to the vicinity of a distal end of the inner tube 150 through a well-known method such as welding.

The vicinity of a proximal end of the inner tube 150 is liquid-tightly and airtightly bonded to an opening portion for connection 162 which is formed at a predetermined position of the outer tube 160. The guide wire 190 is insertable/movable through the guide wire lumen 151 because there is a distal end opening portion 153 (i.e., an opening that communicates with the exterior of the device) at the distal end of the inner tube 150 and a proximal end opening portion 155 at the proximal end of the inner tube 150 respectively as an inlet or an outlet.

The distal end of the inner tube 150 can include a tip which prevents damage in a biological organ when, for example, the distal end of the balloon catheter 100 comes into contact with a biological organ (such as an inner wall of a blood vessel). The tip can be formed of, for example, a tubular member which is more flexible than the inner tube 150.

As the material constituting the inner tube 150, it is possible to use, for example, polyolefins such as polyethylene, polypropylene, an ethylene-propylene copolymer, and an ethylene-vinyl acetate copolymer, a thermoplastic resin such as soft polyvinyl chloride, various kinds of rubber such as silicone rubber or latex rubber, various elastomers such as a polyurethane elastomer, a polyamide elastomer, and a polyester elastomer, and crystalline plastics such as polyamide, crystalline polyethylene, and crystalline polypropylene. It is also possible to make a material having antithrombogenicity after blending an antithrombotic substance such as heparin, prostaglandins, urokinase, and an arginine derivative with these materials.

The outer tube 160 is formed of a hollow tube material (i.e., a cylindrical or tubularly-shaped material) which extends (i.e., extends proximally) from the vicinity of a proximal portion 115 of the balloon 110 to the hub 170. The proximal portion 115 of the balloon 110 is liquid-tightly and airtightly bonded to the vicinity of a distal end of the outer tube 160 through a well-known method such as welding (i.e., a distal portion of the outer tube 160 is bonded/fixed to the proximal portion 115 of the balloon 110).

As the constituent material of the outer tube 160, it is possible to use the same material as the inner tube 150 material. In addition, it is also possible to coat a portion (for example, the outer surface of the outer tube 160) coming into contact with blood with a substance having antithrombogenicity.

As shown in FIG. 2A, the hub 170 includes a connection section 171 which can be liquid-tightly and airtightly connected to a supply device (not shown in the drawing) such as an indeflator for supplying a pressurization medium. The connection section 171 of the hub 170 can be constituted, for example, using a well-known luer taper which is configured such that a fluid tube or the like can be connected to the connection section 171 and separated from the connection section 171.

The pressurization medium (for example, a physiological saline or a contrast agent) used for expansion of the balloon 110 can be made to flow into the shaft 140 through the connection section 171 of the hub 170. The pressurization medium is supplied to the balloon 110 via the pressurization medium lumen 161.

Next, the configuration of the balloon 110 provided in the balloon catheter 100 will be described. FIG. 1A is an enlarged perspective view showing the balloon 110, FIG. 1B is a cross-sectional view taken along line 1B-1B shown in FIG. 1A, and FIG. 1C is a view showing an enlarged 1C portion identified in FIG. 1B.

As shown in FIG. 1A, the balloon 110 includes an effective expansion portion 111 that is cylindrically shaped (i.e., a straight shape or an extended hollow tubular shape) when being expanded, a distal side tapered portion 113a which is positioned on a distal side of the effective expansion portion 111 (i.e., the distal side tapered portion 113a is distal of the cylindrically-shaped effective expansion portion 111), and a proximal side tapered portion 115a which is positioned on a proximal side of the effective expansion portion 111 (i.e., the proximal side tapered portion 115a is proximal to the cylindrically-shaped effective expansion portion 111).

The effective expansion portion 111 provides an expansion force on a stenosed site formed in a biological lumen. The balloon 110 includes a projection portion 120 formed in the effective expansion portion 111. The projection portion 120 is formed to have a predetermined length along an axial direction (Y-axis direction) of the balloon 110.

Figure 1B:
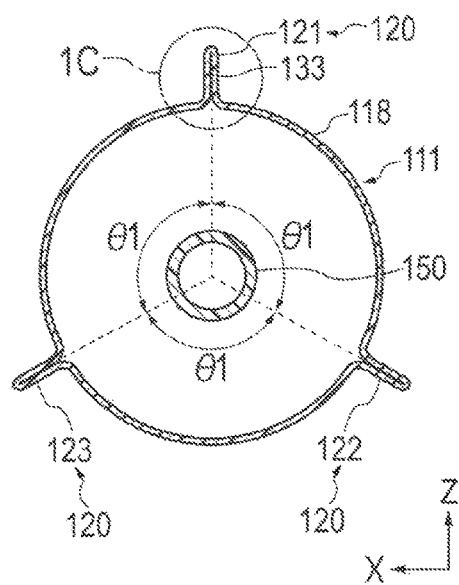
Figure 1C:
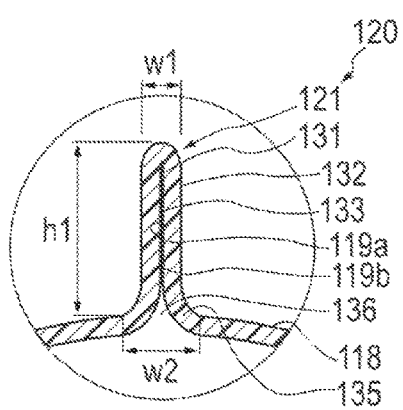

As shown in FIGS. 1B and 1C, the projection portion 120 has a projection shape which protrudes from an outer surface 118 of the balloon 110 outward in a radial direction (radially outward). That is, the projection portion 120 has a projection shape of which a part of the balloon 110 protrudes outward in a radial direction (in a direction away from the inner tube 150). The balloon 110 has three projection portions 121, 122, and 123 formed at positions different from each other in a circumferential direction of the balloon 110 (i.e., spaced apart from one another in the circumferential direction).

For the convenience of description, the respective projection portions 121, 122, and 123 are referred to here as the first projection portion 121, the second projection portion 122, and the third projection portion 123. The projection portion 120 is a collective term for the projection portions 121, 122, and 123. The projection portions 121, 122, and 123 have substantially the same configuration as each other. Therefore, only the configuration of the first projection portion 121 will be described whereas the description of the other projection portions 122 and 123 will not be repeated.

As shown in FIG. 1C, the first projection portion 121 is configured to protrude a part of the balloon 110 (i.e., a portion of the balloon itself protrudes/forms the projection portion 121) by forming a welded portion 133, in which adjacent inner surfaces 119a and 119b are at least partially welded to each other. These inner surfaces 119a, 119b are at least partially welded together in a portion in which the inner surfaces 119a and 119b of the balloon 110 are made to face each other. Specifically, the adjacent inner surfaces 119a and 119b of the balloon 110 are welded such that a portion, which is made to protrude by drawing a part of the balloon 110 outward in the radial direction is formed, and the projection shape of the protruding portion is maintained. In other words, as illustrated in FIG. 1C, the projection portion includes first and second parts of the balloon so that the inner surface of the first part of the balloon faces the inner surface of the second part of the balloon, the first and second parts of the balloon projecting radially outwardly away from parts of the balloon immediately adjacent the first and second parts. In this manner, the first projection portion 121 is constituted by the part of the balloon 110 (i.e., the balloon 110 is an undivided, unitary structure such that the first projection portion 121 is a portion that is formed at the same time that the balloon 110 is formed).

The welded portion 133 forms a distal portion 131 of the first projection portion 121 positioned outside in the radial direction. The welded portion 133 is formed to have a predetermined length along the radial direction from the distal portion 131. The inner surfaces 119a and 119b included in the first projection portion 121 are closely adhered to each other in a state where there is no gap between both inner surfaces (i.e., the surfaces are in contact and adhered to one another) along a predetermined range on the distal portion 131 side.

The welded portion 133 is not formed in an end portion (hereinafter, also referred to as a "base portion") 135 positioned radially inward (i.e., inward in the radial direction relative to the distal portion 131) of the first projection portion 121. For this reason, the inner surfaces 119a and 119b are separated from each other in the vicinity of the base portion 135 (i.e., the inner surfaces 119a, 119b are not in contact with one another at the base portion 135, or in other words, are spaced apart). This base portion 135 constitutes a wide width portion in which the distance between the adjacent inner surfaces 119a and 119b is gradually expanded inward in the radial direction (i.e., the gap between the inner surfaces 119, 119b increases as the radial distance from the shaft 140 decreases).

In the vicinity of a boundary between the projection portion 120 and an internal space (a space into which a pressurization medium flows) of the balloon 110, the inner surfaces 119a and 119b are separated from each other (i.e., spaced apart). A groove 136 which communicates with the internal space of the balloon 110 is formed in the vicinity of this boundary.

The groove 136 extends along the axial direction of the balloon 110 similarly to the projection portion 120. When the balloon 110 contracts (i.e., deflates or shrinks), the entirety of the balloon 110 contracts while the projection portion 120 moves inward to the shaft 140 (inner tube 150) so as to be guided thereto, with the groove 136 as a starting point. For this reason, even in a case where the balloon 110 is expanded and contracted many times (i.e., is cycled between being inflated and deflated many time), it is difficult to cause variations in positions at which the projection portion 120 is disposed. In other words, the reproducibility of the shape of the balloon while being contracted becomes high. When the expansion and contraction of the balloon 110 is repeatedly performed to treat a plurality of different kinds of lesion areas, the properties of the balloon 110 passing through stenosed sites again become favorable.

The portion positioned further on the distal portion 131 side than the base portion 135 (i.e., distal to the base portion 135) constitutes a columnar portion 132 provided with a substantially constant width. The most distal end of this columnar portion 132 can possess, for example, a cross-sectional shape which is curved as shown in the drawing. However, the shape of the most distal end is not particularly limited, and it is possible to form a tapered shape which is tapered toward the distal end or to form a rectangular cross-sectional shape.

As shown in FIG. 4C, the balloon 110 is folded after manufacturing the balloon catheter 100 and is wound around the inner tube 150 provided in the shaft 140. The balloon 110 is inserted into a protection sheath 195 with the diameter of the balloon being reduced by being wound around the inner tube 150 before use of the balloon catheter 100.

As shown in FIG. 4B, each of the projection portions 121, 122, and 123 is formed at an end portion 137a of a blade portion 137, is formed when the balloon 110 is folded, and is wound around the inner tube 150. The blade portion 137 is formed on the balloon 110, is wound around the inner tube 150 in a circumferential direction, and is provided with a blade shape extending in a radial direction (i.e., the blade portion 137 protrudes radially outwardly). The blade shape of the blade portion 137 is created by closely adhering the inner surfaces of the balloon 110 to each other. The end portion 137a of the blade portion 137 is the end portion (distal portion) positioned in a direction away from the inner tube 150 (i.e., the radially outward portion of the blade portion 137).

The method for forming the welded portion 133 can be appropriately selected according to the material of the balloon 110. For example, it is possible to employ well-known welding methods such as laser welding, high frequency welding, and thermal welding which are performed using various heat sources.

The welded portion 133 may be formed by, for example, welding only the inner surfaces 119a and 119b of the balloon 110. Alternatively, the weld portion 133 may be formed by welding the entire portion constituting the projection portion 120 in the balloon 110. In the embodiment illustrated in FIG. 4B, the welded portion 133 is formed by welding only the inner surfaces 119a and 119b in order to prevent the durability of the projection portion 120 from being impaired (i.e., to ensure the projection portion 120 is durable) due to decreased thickness of the balloon 110 at the projection portion 120. For example, laser welding can be employed as the method for welding only the inner surfaces 119a and 119b. When performing laser welding, it is possible to accurately weld only the inner surfaces 119a and 119b by setting the focal position of a laser in the vicinity of the inner surfaces 119a and 119b (so that the focused laser does not weld any unintended surfaces/areas of the balloon 110).

The welded portion 133 is formed by applying a fixing force to maintain a part of the balloon 110 in a projection shape (i.e., so that the part of the balloon protrudes outward in a projection shape). This fixing force is applied to each of the adjacent inner surfaces 119a and 119b. The position or the range (the position and the range of welding the inner surfaces 119a and 119b to each other) of forming the welded portion 133 can be appropriately changed as long as the shape of the projection portion 120 is not impaired.

As illustrated in FIG. 1C, a height dimension h1 is the distance from the outer surface of the base portion 135 (i.e., the distance from the outer surface of the balloon at the base portion 135) to the outer surface of the distal portion 131 of the projection portion 120. The height dimension h1 can be, for example, 0.1 mm to 2.0 mm. The width dimension w1 of the columnar portion 132 can be, for example, 0.02 mm to 0.2 mm. The width dimension w2 of the base portion 135 can be, for example, 0.1 mm to 2.0 mm.

As illustrated in FIG. 1A, a length L1 of the projection portion 120 in the axial direction can be, for example, 5 mm to 300 mm.

Note that each dimension of the projection portion 120 can be appropriately changed as long as the expansion performance of using the balloon 110 makes the projection portion 120 bite into a stenosed site when the balloon 110 is expanded. However, the projection portion 120 is not limited to each of the dimension examples discussed above.

The constituent material of the balloon 110 is not particularly limited as long as it is possible to form the projection portion 120. As the constituent material, it is possible to use, for example, polyolefins such as polyethylene, polypropylene, and an ethylene-propylene copolymer, polyester such as polyethylene terephthalate, thermoplastic resins such as polyvinyl chloride, an ethylene-vinyl acetate copolymer, a cross-linked ethylene-vinyl acetate copolymer, and polyurethane, polyamide, polyamide elastomer, polystyrene elastomer, silicone rubber, and latex rubber.

The projection portion 120 formed in the balloon 110 can be formed of the same material as the material of the balloon 110 (i.e., the balloon 110 and the projection portion 120 are integrally formed in one piece at the same time such that the balloon is a single, unitary structure). It is thus possible to adjust the flexibility of the projection portion 120 by, for example, appropriately selecting the constituent material of the balloon 110 (i.e., by forming the balloon 110 out of a flexible material). In addition, it is also possible to adjust the flexibility of the projection portion 120 by adjusting the thickness of the balloon 110.

In a case of forming a plurality of projection portions 121, 122, and 123 on one balloon 110 as shown in the balloon catheter 100 according to the embodiment illustrated in FIGS. 1A-1C, it is preferable that the projection portions 121, 122, and 123 are arranged, for example, with equal intervals between the projection portions 121, 122, and 123 in the circumferential direction. As shown in FIG. 1B, the balloon catheter 100 has an angle difference θ1 of 120° between center positions of each of the projection portions 121, 122, and 123 (i.e., the projection portions 121, 122, and 123 are circumferentially spaced apart by θ1 degrees). By disposing the projection portions 121, 122, and 123 at equal intervals in the circumferential direction (i.e., at) 120° in this manner, it is possible to make the projection portions 121, 122, and 123 bite (i.e., cut into or penetrate the surface of the stenosed site) at equal positions in the circumferential direction of a stenosed site when widening the stenosed site. Therefore, it is possible to more efficiently widen the stenosed site.

In the embodiment depicted in FIGS. 1A-1C, an example is shown in which the three projection portions 120 are formed in the effective expansion portion 111 of the balloon 110. However, the balloon catheter disclosed here is not particularly limited as long as the number of projection portions 120 is greater than or equal to one (i.e., there must be at least one projection portion 120). When there are two or more projection portions 120, it is possible to arbitrarily set the intervals 61 between the projection portions 120 in the circumferential direction of the balloon 110. Equal intervals may or may not be provided between the projection portions 120. In addition, when there are a plurality of projection portions 120, the dimensions such as the height, the width, and the length in the axial direction, the shape, or the like may differ for each projection portion 120 (i.e., the projection portions may have different dimensions from one another).

Next, a method for manufacturing the balloon 110 and a method for forming the blade portion 137 on the balloon 110 will be described with reference to FIGS. 3A-4C. FIGS. 3A-4C are views simply showing main parts of a device used in each manufacturing step to form the balloon 110, an operation step of forming the blade portion 137, and each step.

First, as shown in FIG. 3A, the manufacturing method includes a balloon molding step of molding a tubular balloon material (parison) 110a in the balloon 110 in a predetermined shape. The balloon material 110a can be arbitrarily selected from, for example, the above-described materials exemplified as the constituent material of the balloon.

The balloon molding step can be performed through blow-molding using a predetermined balloon mold 710. The balloon mold 710 may be, for example, a mold including three separation molds 711, 712, and 713 forming a predetermined molding surface 715 through closing the molds (i.e., the predetermined molding surface 715 is formed when the three separation molds 711, 712, and 713 are closed).

When the separation molds 711, 712, and 713 are closed, a ridgeline portion 715a which molds the effective expansion portion 111 and/or the tapered portions 113a and 115a of the balloon 110 is formed. The balloon mold 710 also forms a concave portion 715b when the balloon mold 710 is closed. The concave portion 715b molds an inner surface-opposed portion 119 (refer to FIG. 3B), in which the inner surfaces 119a and 119b of the balloon 110 face each other in a portion in which the projection portion 120 is formed in the balloon 110.

When blow-molding is performed using the balloon mold 710, it is possible to form the tubular balloon material 110a into a predetermined balloon shape. In addition, it is possible to mold an inner surface-opposed portion 119 in the balloon 110 (as shown in FIG. 3B) by performing the blow-molding using the balloon mold 710. By molding the inner surface-opposed portion 119 in the balloon 110 in this manner when molding the tubular balloon material 110a into the balloon 110, it is possible to reduce the number of steps compared to molding the balloon 110 and then separately molding of the inner surface-opposed portion 119 in an additional step.

Note that the portion which molds the inner surface-opposed portion 119 in the balloon 110 can be set in advance at a position at which the end portion 137a of the blade portion 137 is formed (e.g., as illustrated in FIG. 4B).

After the balloon molding step is completed, the balloon 110 is taken out of the balloon mold 710.

Next, as shown in FIG. 3C, the projection portion 120 is formed to protrude (i.e., radially outward) from the outer surface 118 of the balloon 110 by welding the adjacent inner surfaces 119a and 119b in the inner surface-opposed portion 119 along the axial direction of the balloon 110 (i.e., the weld bead extends in the axial direction along/between the adjacent inner surfaces 119a and 119b). When performing the welding, it is possible to use a tool or the like which clamps the outer surface 118 of the balloon 110 to hold the inner surfaces 119a and 119b in a state of being closely adhered to each other.

The balloon 110 can be manufactured through the above-described step. After manufacturing the balloon 110, the balloon catheter 100 is assembled by bonding the balloon 110 to the distal portion of the shaft 140 through welding or the like.

After assembling the balloon catheter 100, the balloon 110 is wound around the inner tube 150 by folding the balloon 110 (e.g., as illustrated in FIG. 3B with the arrows indicating the folding direction).

When performing the operation of folding the balloon 110, a blade portion-forming step is performed in which the blade portion 137 is formed on the balloon 110 as shown in FIG. 4A. The blade portion 137 can be formed using a predetermined lapping device 770.

The lapping device 770 includes three pressing members 771, 772, and 773. The pressing members 771, 772, and 773 are configured to approach one another and separate from one another. As shown in FIG. 4A, the pressing members 771, 772, and 773 form a hole portion 775a into which the inner tube 150 is inserted and a blade shape-imparting portion 775b extending from the hole portion 775a in the radial direction. The pressing members form the hole portion 775a and the blade shape-imparting portion 775b by approaching to and being combined with each other (i.e., collectively defining the portions 775a, 775b). In addition, heating means (not shown in the drawing) for heating the balloon 110 is installed in the pressing members 771, 772, and 773. For example, a well-known heating wire can be used as the heating means.

The lapping device 770 presses/pushes the outer circumference of the balloon 110 radially inward from three directions by moving the pressing members 771, 772, and 773 closer to each other in a state in which the inner tube 150 is disposed in the vicinity of the center portion of the lapping device 770. The lapping device 770 heats the balloon 110 when the lapping device 770 presses/pushes the outer surface of the balloon 110 in this manner. In the portion pinched by the blade shape-imparting portion 775b in the balloon 110, the inner surfaces are closely adhered to each other so as to overlap each other. Evacuation is performed through the outer tube 160 while this state is maintained. Thereafter, the balloon 110 is taken out after separating the pressing members 771, 772, and 773 from each other.

As shown in FIG. 4B, the blade portion 137 is formed on the balloon 110. The projection portion 120 (which has been formed during the manufacturing of the balloon 110) is disposed at the end portion 137a of the blade portion 137.

Next, the blade portion 137 is wound around the outer circumference of the inner tube 150 of the shaft 140 (as denoted by the arrows in FIG. 4B demonstrating the winding in the circumferential direction). When winding the blade portion 137, the end portion 137a of the blade portion 137 becomes disposed along (i.e., in contact with) the outer circumference surface of the inner tube 150. By winding the blade portion 137 in this manner, it is possible to prevent the projection portion 120 formed at the end portion 137a of the blade portion 137 from protruding on the outer surface side of the balloon 110. Accordingly, it is possible to prevent the projection portion 120 from coming into contact with the inner surface of a biological lumen when moving the balloon 110 in the biological lumen. It is thus possible to reduce the load applied to the biological lumen. In addition, as shown in FIG. 4C, the projection portion 120 formed at the end portion 137a of the blade portion 137 is not covered by the blade portion 137 when the blade portion 137 is wound around the outer circumference of the inner tube 150 of the shaft 140. This helps prevent the outer surface 118 of the balloon 110 from being damaged by the projection portion 120.

After the operation of winding the blade portion 137 is completed, the balloon 110 is inserted into a predetermined protection sheath 195 to cover the balloon 110 with the protection sheath 195 (i.e., the balloon 110 is inside of the protection sheath 195 so that it is unexposed). The projection portion 120 formed at the end portion 137a of the blade portion 137 includes the welded portion 133, and therefore, is made to be hard compared to other sites which are comparatively flexible. Therefore, the sliding resistance which acts between the balloon 110 and the inner surface of the protection sheath 195 is decreased when the balloon 110 is inserted into the protection sheath 195. Accordingly, it is possible to smoothly perform the insertion operation of the balloon 110.

Next, an action of the balloon catheter 100 according to the present embodiment will be described (i.e., a description of one example of using the balloon catheter 100 follows).

When performing a technique of widening a stenosed site using the balloon 110, the projection portion 120 formed on the balloon 110 has a function of causing dissociation (crack or breaking up) of the stenosed site by biting into the stenosed site (i.e., cutting into or penetrating the wall of the stenosed site) similarly to a blade provided in a blade-attached balloon catheter in the related art. The projection portion 120 makes it possible to improve the performance of expanding the balloon 110 with respect to the stenosed site.

As described above, the projection portion 120 is a part of the balloon 110. For this reason, it is possible to prevent problems such as a decrease in flexibility of the balloon 110 (which occurs when a blade formed of a member different from the balloon 110 is installed) or detachment of the blade from the balloon 110. The manufacturing process of the balloon 110 disclosed here becomes simpler and the number of parts required can be decreased compared to the case of separately installing a blade. Therefore, it is possible to reduce manufacturing costs.

Since the balloon 110 and the projection portion 120 are formed of the same material, it is possible to suitably prevent damage to the outer surface 118 of the balloon 110 during folding of the balloon 110 and/or during operation of the balloon 110 in a biological lumen.

In addition, the welded portion 133 is formed at the distal portion 131 of the projection portion 120 which is positioned outward in the radial direction (i.e., the welded portion 133 is at the radial outward portion of the projection portion 120). Therefore, it is possible to prevent the distal portion 131 of the projection portion 120 from being excessively flexible. Accordingly, it is possible to make the distal portion 131 of the projection portion 120 easily bite into the stenosed site according to expansion deformation of the balloon 110 (i.e., the distal portion 131 of the projection portion 120 is more rigid than the balloon 110 so that it can firmly contact/cut/penetrate the stenosed site). Therefore, the performance of expanding the balloon 110 is further improved.

In addition, since the projection portion 120 has the wide width portion 135 in which the distance between the adjacent inner surfaces 119a and 119b is gradually expanded inward in the radial direction (i.e., the distance between the inner surfaces 119a, 119b of the projection portion 120 increases as the radial distance from the center of the balloon 110 decreases), the projection portion 120 can be deformed along the outer surface 118 of the balloon 110 (i.e., to contact/lay against the outer surface 118 of the balloon 110) with the wide width portion 135 as a starting point when folding the balloon 110 to be wound around the shaft 140 (when making the expanded balloon 110 to be contracted). Accordingly, it is possible to reduce the diameter of the balloon when being folded. Therefore, passing properties (i.e., maneuverability) with respect to the stenosed site is further improved. In addition, since the projection portion 120 has the wide width portion 135 which becomes a starting point when the balloon 110 is folded, even when the operations of expanding and contracting the balloon 110 are performed multiple times, it is possible to reduce the diameter of the balloon when being folded. For this reason, passing properties with respect to the stenosed site are further improved.

By forming the projection portion 120 at the end portion 137a of the blade portion 137, it is possible to prevent the projection portion 120 from protruding on the outer surface side of the balloon 110 when the balloon 110 is folded and wound around the shaft 140. Accordingly, it is possible to prevent the projection portion 120 from coming into contact with the inner surface of a biological lumen when moving the balloon 110 in the biological lumen. It is thus possible to reduce the load applied to the biological lumen.

In addition, it is possible to provide a suitable manufacturing method for manufacturing the balloon 110 of the balloon catheter 100. Specifically, it is possible to provide a method for manufacturing a balloon which includes: a balloon molding step of molding the tubular balloon material 110a in the balloon 110 having a predetermined shape; and a projection portion-forming step of making a part of the balloon 110 protrude outward in the radial direction by mutually welding at least a part of the adjacent inner surfaces 119a and 119b in a portion in which the inner surfaces 119a and 119b of the balloon 110 are made to face each other, to form at least one projection portion 120 having a predetermined length along the axial direction of the balloon 110.

According to manufacturing method of the present embodiment, it is possible to manufacture the balloon 110 on which the projection portion 120 (which improves the expansion performance with respect to the stenosed site) is formed. In addition, according to the method, it is possible to manufacture a balloon through a simple manufacturing step and to decrease the number of parts compared to when a blade is separately installed on the balloon 110. Therefore, it is possible to reduce the manufacturing costs of the balloon 110.

In the balloon molding step (i.e., molding the tubular balloon material into the balloon), the inner surfaces 119a and 119b of the balloon 110 are disposed to face each other in a portion in which the projection portion 120 is formed in the balloon 110. The inner surfaces 119a and 119b form the inner surface opposed portion 119. Therefore, it is possible to reduce the number of steps compared to the case of performing the molding of the balloon 110 and the molding of the inner surface-opposed portion 119 in separate steps. Thus, the manufacturing operation becomes simpler.

The blade portion-forming step of forming the projection portion 120 at the end portion 137a of the blade portion 137 makes is possible to prevent the projection portion 120 formed at the end portion 137a of the blade portion 137 from protruding on the outer surface side of the balloon 110. Accordingly, it is possible to provide the balloon 110 which can reduce the load applied to a biological lumen when moving the balloon in the biological lumen.

Second Embodiment

Figure 5A:
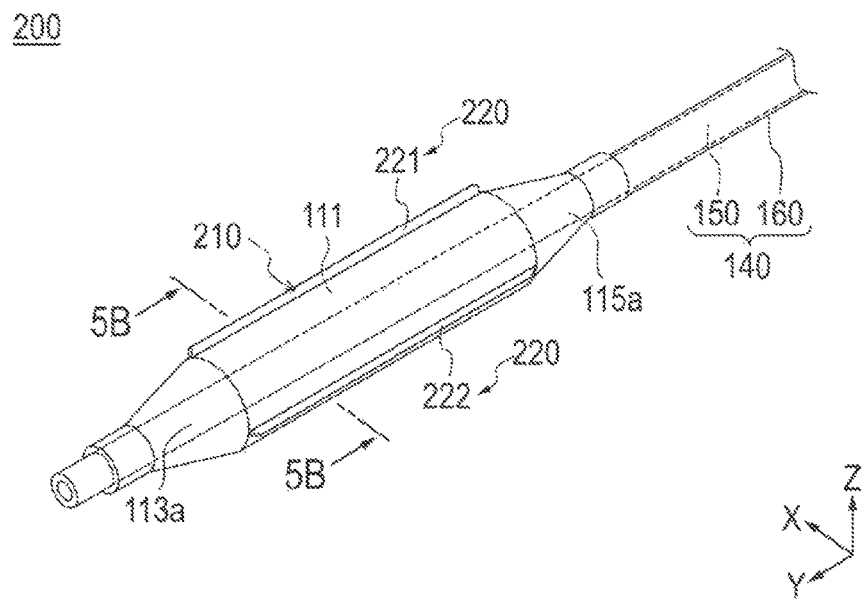
FIGS. 5A-5C are views showing a balloon catheter according to a second embodiment.
Figure 5B:
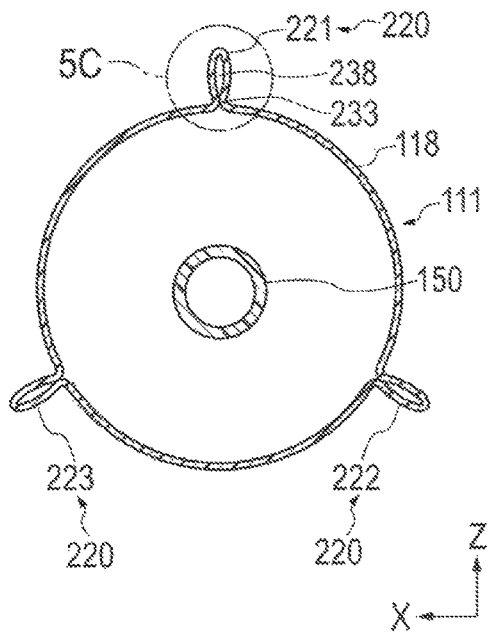
Figure 5C:
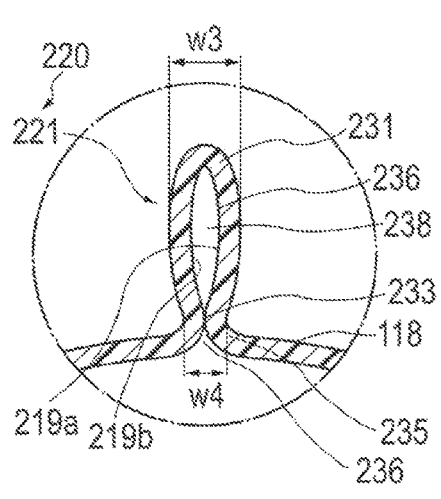

Next, a balloon catheter according to a second embodiment of the present invention will be described with reference to FIGS. 5A-5C. FIG. 5A is a perspective view showing an inflated balloon, FIG. 5B is a cross-sectional view taken along line 5B-5B shown in FIG. 5A, and FIG. 5C is a view showing an enlarged 5C portion identified in FIG. 5B. The description of the members or the configurations which have already been described in the description of the balloon catheter according to the first embodiment will not be repeated.

In a balloon catheter 200 according to a second embodiment, the configuration of a projection portion 220 formed on a balloon 210 is different from that of the balloon 110 according to the first embodiment. Specifically, the welded portion 133 of the projection portion 120 on the balloon 110 of the first embodiment is formed at the distal portion 131 of the projection portion (i.e., the projection portion 120 is welded at its radially outer edge). In contrast, in the projection portion 220 formed on the balloon 210 according to the embodiment illustrated in FIGS. 5A-5C, a welded portion is not formed at a distal portion 231.

Three projection portions (i.e., the first projection portion 221 the second projection 222, and the third projection 223) are formed on the balloon 210. The projection portions 221, 222, and 223 have substantially the same configuration as each other. Therefore, only the configuration of the first projection portion 221 will be described whereas the description of the other projection portions 222 and 223 will not be repeated. Note that the projection portion 220 is a collective term for the projection portions 221, 222, and 223.

As shown in FIG. 5C, the first projection portion 221 has a gap portion 238 which is formed between the adjacent inner surfaces 219a and 219b. The gap portion 238 is formed further outside (on the distal portion 231 side or radially outward of the welded portion 233) in the radial direction than the welded portion 233. The gap portion 238 is formed such that the inner surfaces 219a and 219b, which are adjacent on the distal portion 231 side, are not welded to each other. This portion remains a non-welded portion. Note that the gap portion 238 is formed such that a fluid (pressurization medium) for expansion does not flow into the gap portion 238 when the balloon 210 is expanded using the fluid for expansion or the like. Accordingly, when the balloon 210 is expanded, it is possible to prevent damage on the balloon 210 due to pressure during the expansion.

The gap portion 238 formed in the first projection portion 221 has an elliptical cross-sectional shape in which the major axis direction extends along the radial direction (i.e., the axis of the gap portion 238 in the radial direction is longer than the axis of the gap portion 238 in the circumferential direction). In the vicinity of a boundary of the first projection portion 221 and the internal space of the balloon 210, a groove 236 is formed which becomes a starting point of contraction deformation when the balloon 210 is contracted.

The width of at least a part of a portion, in which the gap portion 238 is formed in the first projection portion 221, along the circumferential direction of the balloon 210 is formed to be wider than that of a portion in which the welded portion 233 is formed (i.e., the width of at least part of the gap portion 238 is wider than the width of the projection portion 221 at the welded portion 233 in a circumferential direction of the balloon 210). In the present embodiment, a dimension w3 of a portion in which the width of the gap portion 238 becomes the maximum is formed to be greater than a dimension w4 of the width of the portion in which the welded portion 233 is formed (e.g., the width at or near center of the projection portion 221 is greater than the width w4 at the base of the projection portion 221).

The projection portion 220 can be formed by, for example, the following procedure.

First, an inner surface-opposed portion is formed in the balloon 210 as described in the first embodiment (refer to FIG. 3B). Next, the welded portion 233 is formed in the vicinity of a base portion 235 of the projection portion 220. With such a procedure, it is possible to constitute the projection portion 220 using a part of the balloon 210 (i.e., part of the balloon 210 itself forms the projection portion 220).

As described above, in the balloon catheter 200 according to the second embodiment, the projection portion 220 possesses the gap portion 238 between the adjacent inner surfaces 219a and 219b. This gap portion 238 is formed further outside in the radial direction than the welded portion 233. By providing the gap portion 238 in the projection portion 220, it is possible to adjust the flexibility of the projection portion 220. For example, by forming the projection portion 220 to be comparatively flexible, it is possible to reduce the load applied to a biological organ when moving the balloon 210 in a biological lumen. Furthermore, when winding a balloon around the shaft 140, the projection portion 220 is flexibly deformed along the outer circumference surface of the shaft 140. Therefore, it is possible to reduce the diameter of the balloon during contraction.

In addition, the dimension of the width of at least a part of a portion, in which the gap portion 238 is formed in the projection portion 220, along the circumferential direction of the balloon 210 is larger than that of a portion in which the welded portion 233 is formed. For this reason, the dimension of the width of the gap portion 238 (i.e., the distance between the adjacent inner surfaces 219a and 219b) can be set to be relatively large. It is thus possible to provide the projection portion 220 with predetermined flexibility.

The cross-sectional shape of the gap portion 238 is not limited to the elliptical shape shown in the drawing, and can be, for example, a round shape. In addition, the width of the gap portion 238, the length of the gap portion 238 in the radial direction, and the size (capacity) of the gap portion 238 or the like is not particularly limited.

Third Embodiment

Figure 6A:
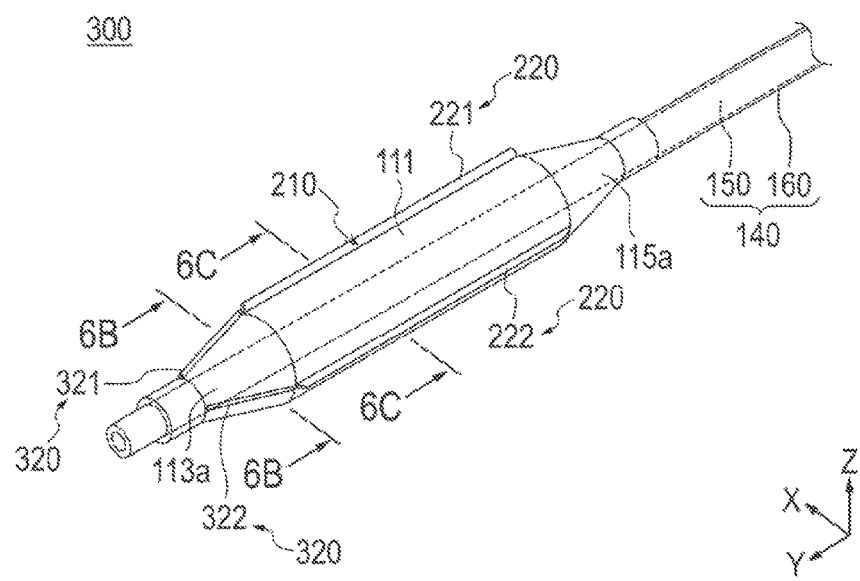
FIGS. 6A-6C are views showing a balloon catheter according to a third embodiment.
Figure 6B:
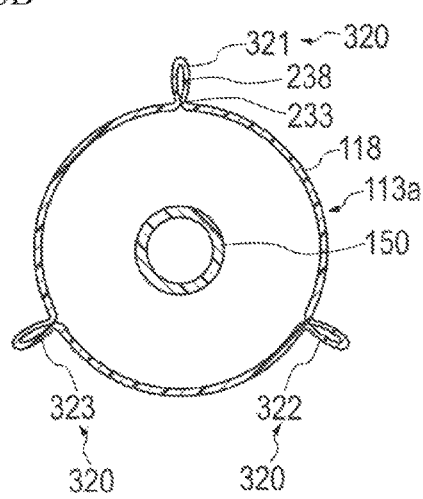
Figure 6C:
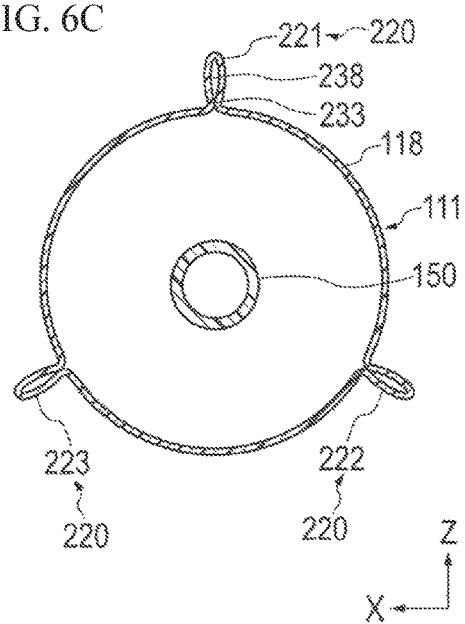

Next, a balloon catheter according to a third embodiment of the present invention will be described with reference to FIGS. 6A-6C. FIG. 6A is a perspective view showing an enlarged balloon, FIG. 6B is a cross-sectional view taken along line 6B-6B shown in FIG. 6A, and FIG. 6C is a cross-sectional view taken along line 6C-6C shown in FIG. 6A. The description of the members or the configurations which have already been described in the description of the balloon catheters according to the above-described embodiments will not be repeated.

The balloon catheter 300 according to the third embodiment includes a distal side tapered portion 113a, which is positioned on a distal side of the effective expansion portion 111 of a balloon 310. The distal side tapered portion 113a possesses an outer diameter that is gradually reduced toward the distal side (i.e., the diameter gradually decreases in the distal direction). The distal side tapered portion 113a is also provided with a projection portion 320. The balloon catheter 300 according to the third embodiment is different from the above-described balloon catheter 200 according to the second embodiment from such a point.

As shown in FIG. 6B, three projection portions (i.e., first projection portion 321, second projection portion 322, and third projection portion 323) are formed on the distal side tapered portion 113a of the balloon 310. The projection portions 321, 322, and 323 have substantially the same configuration as each other. In addition, the projection portions 321, 322, and 323 have substantially the same configuration as that of the projection portion 220 described in the second embodiment. Note that the projection portion 320 is a collective term for the projection portions 321, 322, and 323.

As shown in FIG. 6C, three projection portions of the first to third projection portions 221, 222, and 223 are formed in the effective expansion portion 111 of the balloon 310. Note that the projection portion 220 formed in the effective expansion portion 111 has a larger height dimension in the radial direction than that of the projection portion 320 formed on the distal side tapered portion 113a (i.e., the distance that the projection portion 220 extends radially outward from the effective expansion portion 111 is greater than the distance that the projection portion 320 extends from the distal side tapered portion 113a).

In the balloon catheter 300 according to the third embodiment, the distal side tapered portion 113a of the balloon 310 is also provided with the projection portion 320. The rigidity of the distal side tapered portion 113a is partially enhanced by forming the projection portion 320. The sliding resistance acting between the stenosed site and the distal side tapered portion 113a is thus suppressed when inserting the balloon 310 into a stenosed site. Accordingly, passing properties (i.e., maneuverability) of the balloon 310 is further improved.

Note that it is also possible to form the projection portion 120 described in the first embodiment on the distal side tapered portion 113a.

The first to third projection portions 321, 322, and 323 of the distal side tapered portion are not limited to possessing the shape illustrated in FIG. 6A. For example, the first projection portion 321 of the distal side tapered portion 113a may be formed continuously with the first projection portion 221 of the effective expansion portion 111. In addition, the second projection portion 322 of the distal side tapered portion 113a may be formed continuously with the second projection portion 222 of the effective expansion portion 111. The third projection portion 323 of the distal side tapered portion 113a may also be formed continuously with the third projection portion 223 of the effective expansion portion 111.

Fourth Embodiment

Figure 7A:
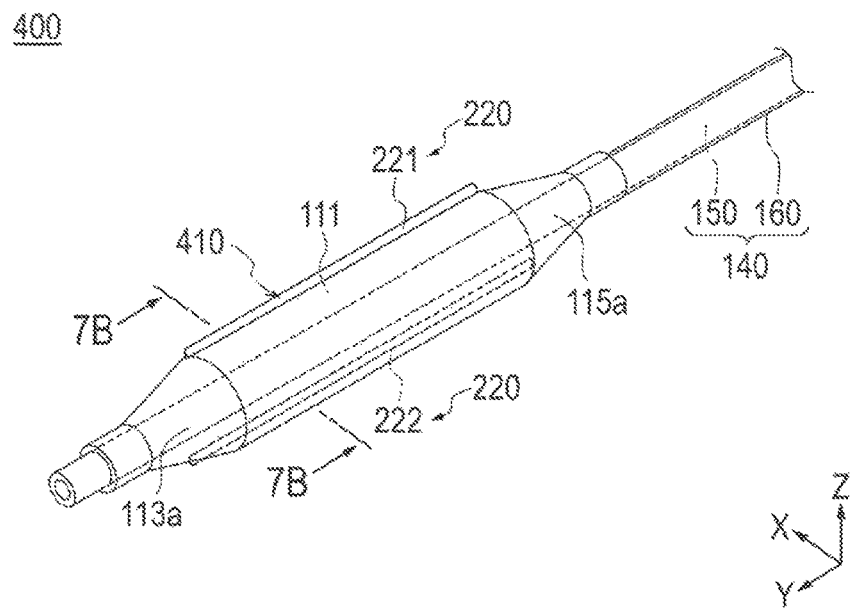
FIGS. 7A and 7B are views showing a balloon catheter according to a fourth embodiment.
Figure 7B:
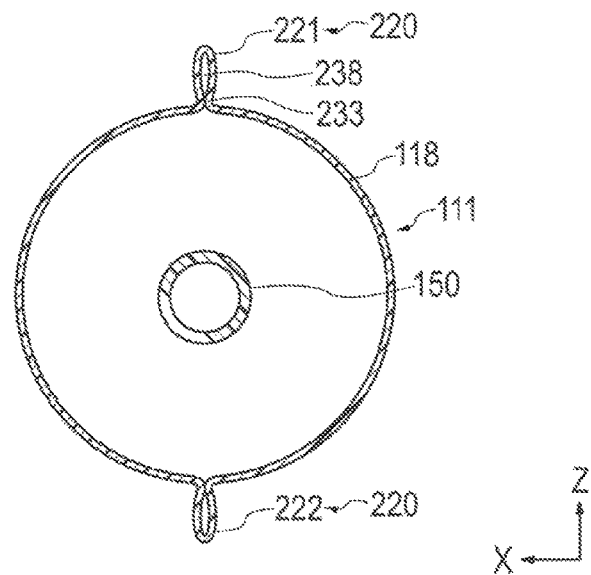

Next, a balloon catheter according to a fourth embodiment will be described with reference to FIGS. 7A and 7B. FIG. 7A is a perspective view showing an enlarged balloon and FIG. 7B is a cross-sectional view taken along line 7B-7B shown in FIG. 7A. The description of the members or the configurations which have already been described in the description of the balloon catheters according to the above-described embodiments will not be repeated.

As shown in FIGS. 7A and 7B, it is possible to form, for example, two projection portions 220 in the effective expansion portion 111 of a balloon 410.

An angle difference of 180° is provided between the first projection portion 221 and the second projection portion 222 along a circumferential direction of the balloon 410.

An example of a method for manufacturing the balloon 410 illustrated in FIGS. 7A and 7B will be described with reference to FIGS. 8A and 8B.

Figure 8A:
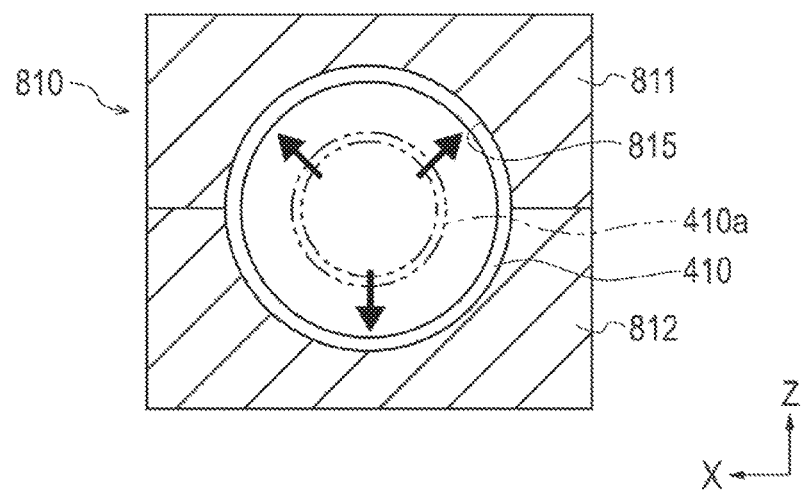
FIGS. 8A and 8B are views for illustrating a manufacturing step of the balloon of the embodiment depicted in FIGS. 7A and 7B.

First, a tubular balloon material 410a is molded into a balloon 410 having a predetermined shape using a balloon mold 810 as shown in FIG. 8A. As the balloon mold 810, it is possible to use a well-known mold for blow-molding provided with a first mold 811 and a second mold 812 which form a molding surface 815 coincident with the shape of the balloon.

A material of which the circumferential length is formed to be longer by the portion of considering the projection portion 220 is used as the tubular balloon material 410a (i.e., an appropriate amount of tubular balloon material 410a is used so that both the balloon 410 and the projection portion 220 can be formed at the same time out of the material). Specifically, a balloon material 410a to which the length which is longer than a required circumferential length is added by the portion of (height of projection portion formed)×2×(number of projection portions formed) as a desired diameter of a balloon is prepared. By adding such a length of tubular balloon material 410a, it is possible to secure a desired diameter of a balloon even in a case of forming the projection portion 220 in a portion in which the inner surfaces of the balloon 410 are made to face to each other.

As shown in FIG. 8A, the balloon 410 is molded by performing the blow-molding using the balloon mold 810.

After the completion of the molding, the balloon 410 is taken out of the balloon mold 810.

Figure 8B:
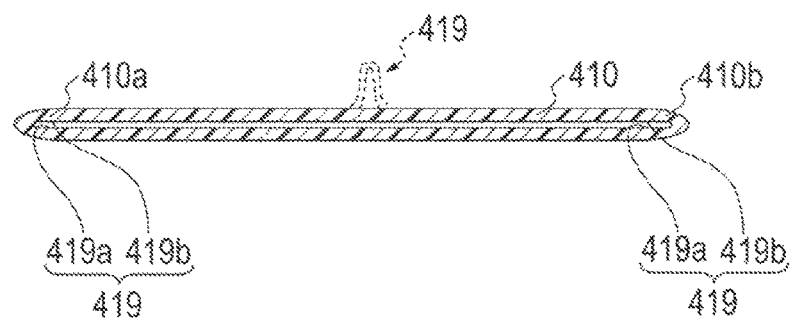

Next, the balloon 410 which has been molded in a circular cross section is shaped in a shield (flat) shape as shown in FIG. 8B. End portions 410a and 410b of the balloon 410 form an inner surface-opposed portion 419 in which inner surfaces 419a and 419b are opposed to each other (i.e., facing one another). It is possible to form the projection portion 220 by welding the inner surfaces 419a and 419b in the inner surface-opposed portion 419. If the projection portion 220 is formed in this manner, it is possible to prevent the wall thickness of the balloon 410 from being reduced in a portion in which the inner surface-opposed portion 419 is formed. Therefore, it is possible to prevent the occurrence of variation in wall thickness in each portion of the balloon 410 (i.e., so that the balloon 410 possesses a uniform wall thickness), and thus, the quality of the balloon 410 is improved.

When a plurality of projection portions 220 are formed, the number of welding operations corresponds to the number of the projection portions 220. In a case of forming greater than or equal to three projection portions 220 through the method described herein, after the welding operation with respect to the end portions 410a and 410b is completed, the inner surface-opposed portion 419 is formed by deforming a part of the balloon 410 so as to be bent as shown by, for example, a dashed line in the drawing. The welding is then performed in this portion. Therefore, it is possible to form the projection portions 220 at desired positions of the balloon 410.

After forming the projection portions 220 on the balloon 410, the shaft 140 is bonded to the balloon 410 while appropriately expanding the balloon 410. Thereafter, blade portions are formed on the balloon 410. The positions at which the projection portions 220 are to be formed can be set to end portions of the blade portions similarly to the balloon 110 described in the first embodiment.

Note that the projection portions 220 can also be formed on the balloon 410 after bonding the balloon 410 to the shaft 140.

In FIG. 8B, the balloon 410 which has been molded in a circular cross section is shaped in a shield (flat) shape, but the manufacturing method disclosed here is not limited to this shape. For example, the balloon may be shaped in a triangular prism shape or a propeller shape. In this case, the inner surface-opposed portion can be formed at a peak of a triangular prism at which the inner surfaces of the balloon face each other or at an end portion of a blade of the propeller shape.

Modification Examples

Next, a balloon 510 according to a modification example and a balloon 610 according to another modification example will be described with reference to FIGS. 9 and 10.

Figure 9:
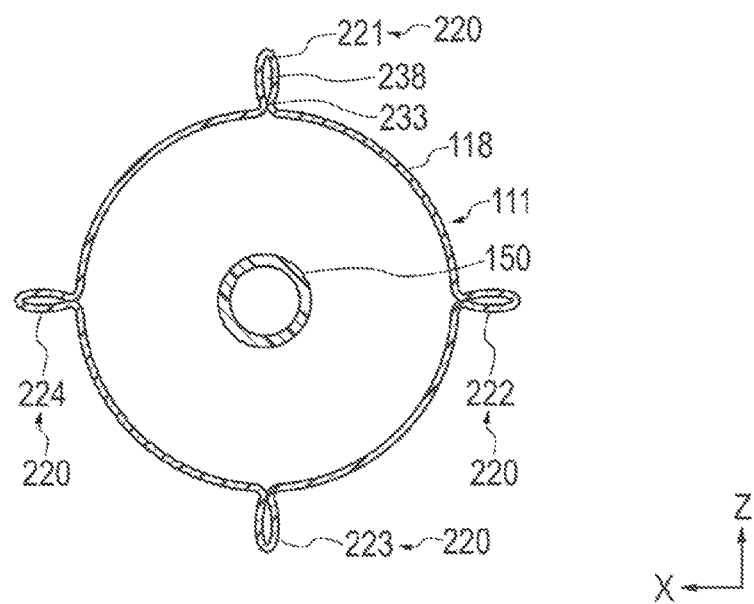
FIG. 9 is a view showing an enlarged cross section of an effective expansion portion of a balloon according to a modification example.

As shown in FIG. 9, it is also possible to form, for example, four projection portions (i.e., first projection portion 221, second projection portion 222, third projection portion 223, and fourth projection portion 224) on one balloon 510. In the case of forming the four projection portions 221, 222, 223, and 224, it is preferable to set an angle difference of 90° between the projection portions 221, 222, 223, and 224 along the circumferential direction of the balloon 510 (i.e., so that the projection portions 221, 222, 223, 224 are equally spaced at angular intervals in the circumferential direction). By setting such an angle difference, it is possible to provide equal intervals between the projection portions 221, 222, 223, and 224. When widening a stenosed site, it is possible to make the projection portions 221, 222, 223, and 224 bite into equal positions in the circumferential direction of the stenosed site, and therefore, it is possible to efficiently widen the stenosed site.

Figure 10:
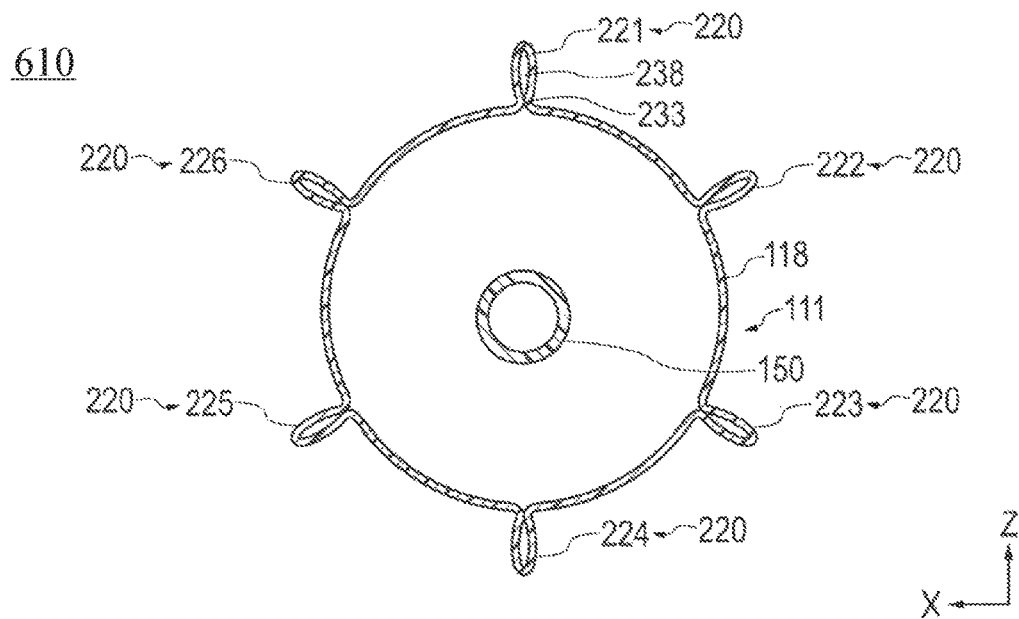
FIG. 10 is a view showing an enlarged cross section of an effective expansion portion of a balloon according to another modification example.

In addition, as shown in FIG. 10, it is also possible to form, for example, six projection portions (i.e., first projection portion 221, second projection portion 222, third projection portion 223, fourth projection portion 224, fifth projection portion 225, and sixth projection portion 226) on one balloon 610. In the case of forming the six projection portions 221, 222, 223, 224, 225, and 226, it is preferable to set an angle difference of 60° between the projection portions 221, 222, 223, 224, 225, and 226 along the circumferential direction of the balloon 610. By setting such an angle difference, it is possible to provide equal intervals between the projection portions 221, 222, 223, 224, 225, and 226 (i.e., so the projection portions 221-226 are equally spaced in angular intervals in the circumferential direction). When widening a stenosed site, it is possible to make the projection portions 221, 222, 223, 224, 225, and 226 bite into equal positions in the circumferential direction of the stenosed site, and therefore, it is possible to efficiently widen the stenosed site.

In the above description, the balloon catheters and the method for manufacturing a balloon have been described using a plurality of embodiments and modification examples. However, the present invention is not limited to only the configurations described in the embodiments and the modification examples, and can be appropriately changed based on the description of Claims.

For example, it is also possible to form one projection portion by mutually welding two or more projection portions which are formed so as to make the projection portions be adjacent to each other along the circumferential direction of a balloon. It is possible to adjust the flexibility or the width of the projection portion depending on the number of projection portions to be welded.

In addition, a projection portion may be fixed by, for example, bending a distal portion side of the projection portion inward in a radial direction and welding the outer surface of the bent portion. The portion which has been bent and superposed is harder than the other portion. Therefore, it is possible to partially adjust flexibility of the projection portion. It is also possible to adjust the height of the projection portion through the bending.

In addition, the number or the shapes of the projection portions, the positions of the projection portions, and the like are not limited to the description in each embodiment so long as at least one projection portion is provided on the effective expansion portion of the balloon to improve the expanding performance of the balloon. For example, it is also possible to intermittently form a plurality of projection portions along an axial direction of a balloon or to dispose projection portions to form a predetermined pattern (such as a spiral pattern) along a circumferential direction of a balloon. It is also possible to form, for example, a projection portion on a distal side tapered portion of a balloon. Another possibility is to alternately form, for example, a plurality of gap portions and welded portions in one projection portion along a radial direction, or to form a gap portion and a welded portion so as to make the gap portion and the welded portion coexist in one projection portion along an axial direction.

In addition, it is possible to form the projection portion (the projection portion in which the inner surfaces at the distal portion are welded) 120 shown in the first embodiment and the projection portion (the projection portion in which the inner surfaces at the distal portion are not welded) 220 shown in the second embodiment in one balloon. For example, it is possible to form the projection portion 220 (which the flexibility is comparatively high or more flexible than the projection portion 120) on a distal side tapered portion and to form the projection portion 120 (which is comparatively hard or more rigid than the projection portion 220) on an effective expansion portion. The projection portion 220 formed on the distal side tapered portion improves insertion properties with respect to a stenosed site and suitably prevents a distal portion of a balloon from applying a load to a biological organ. In contrast, the projection portion 120 formed on the effective expansion portion improves the expansion performance with respect to the stenosed site. In this manner, it is possible to selectively provide the projection portions 120 and 220 in one balloon in combination. Note that it is also possible to form both projection portions 120 and 220 on the effective expansion portion or to form both projection portions 120 and 220 on each of the distal and proximal tapered portions 113*a* and 115*a*.

The balloons which have been described in the embodiments may be manufactured through the manufacturing method (the method in which molding of a balloon and molding of an inner surface-opposed portion are simultaneously performed in one step using a balloon mold) described in the first embodiment, or may be manufactured through the method (the method in which molding of a balloon and formation of an inner surface-opposed portion are performed in separate steps) for manufacturing a balloon described in the fourth embodiment. The manufacturing methods described above, the configuration of a balloon mold, the configuration of a lapping device, or the like is merely an example which is suitably applied to the manufacturing of a balloon. Accordingly, it is also possible to perform the manufacturing of a balloon by applying other methods or devices.

The detailed description above describes a balloon catheter and a method of manufacturing a balloon according to various embodiments representing examples of the inventive balloon catheter and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
a flexible elongated shaft which possesses a distal portion;
a balloon fixed to the distal portion of the shaft and configured to expand and contract, the balloon extending in an axial direction when expanded, the balloon possessing an inner surface;
the balloon comprising an effective expansion portion and at least one projection portion on the effective expansion portion, the effective expansion portion possessing a cylindrical shape when the balloon is expanded and the projection portion extending for a predetermined length along the axial direction of the balloon;
the projection portion comprised of first and second parts of the balloon so that the inner surface of the first part of the balloon faces the inner surface of the second part of the balloon, the first and second parts of the balloon projecting radially outwardly away from parts of the balloon immediately adjacent the first and second parts; and
the inner surfaces of the first part of the balloon being at least partially welded to the inner surface of the second part of the balloon so that the projection portion comprises a welded portion.

2. The balloon catheter according to claim 1,
wherein the welded portion is formed at a distal portion of the projection portion, the distal portion of the projection portion extending outward in the radial direction.

3. The balloon catheter according to claim 1, wherein the projection portion includes a gap between the inner surface of the first part and the inner surface of the second part, and
the gap is radially outward of the welded portion in the radial direction.

4. The balloon catheter according to claim 3, wherein the first and second parts of the balloon possess an outer surface, and
a distance between the outer surface of the first part and the outer surface of the second part at the gap of the projection portion is greater than a distance between the outer surface of the first part and the outer surface of the second part at the welded portion of the projection portion.

5. The balloon catheter according to claim 1, wherein the projection portion comprises a non-welded portion between the inner surface of the first part and the inner surface of the second part, and
a distance between the inner surface of the first part and the inner surface of the second part in the non-welded portion gradually increases as the distance in the radial direction decreases.

6. The balloon catheter according to claim 1,
wherein the balloon possesses a distal side tapered portion on a distal side of the effective expansion portion, the distal tapered portion possessing an outer diameter which gradually decreases toward the distal side, and
wherein the projection portion extends along the distal side tapered portion.

7. A method for manufacturing a balloon catheter balloon, the method comprising:
molding a material into a balloon possessing a predetermined shape and extending in an axial direction;
protruding a part of the balloon outward in a radial direction such that inner surfaces of the part of the balloon face one another; and
welding at least part of the inner surfaces of the part of the balloon to each other to form a projection portion, the projection portion extending for a predetermined length in the axial direction of the balloon.

8. The method for manufacturing the balloon catheter balloon according to claim 7,
wherein the predetermined shape of the balloon comprises a cylindrically shaped body and a distal tapered portion, the distal tapered portion possessing a diameter that gradually decreases towards a distal-most end in the axial direction.

9. The method for manufacturing the balloon catheter balloon according to claim 7, the method further comprising:
forming a blade portion on the balloon, the blade portion comprising an end portion, and
wherein the end portion of the blade portion is the projection portion.

10. The method for manufacturing the balloon catheter balloon according to claim 9, the method further comprising winding the blade portion of the balloon around a shaft.

11. The method for manufacturing the balloon catheter balloon according to claim 8, wherein the projection portion is formed to extend along an entire axial extent of the cylindrically shaped body of the balloon.

12. The method for manufacturing the balloon catheter balloon according to claim 11, the method further comprising:

forming the projection portion on the distal tapered portion of the balloon.

13. The method for manufacturing the balloon catheter balloon according to claim 11, wherein the molding and the protruding are at the same time.

14. A balloon catheter comprising:

a flexible elongated shaft which possesses a distal portion;

a balloon fixed to the distal portion of the elongated shaft, the balloon configured to expand outward in a radial direction and contract inward in the radial direction, the balloon possessing an outer surface;

the balloon comprising an effective expansion portion which is cylindrically shaped when the balloon is expanded;

the balloon comprising at least one projection portion protruding radially outward, the at least one projection portion extending radially outward beyond the effective expansion portion when the balloon is expanded;

the at least one projection portion comprising inner surfaces that face one another, the inner surfaces of the projection portion that face one another being at least partially welded together; and the entire balloon being integrally formed in one piece at the same time such that the effective expansion portion and the at least one projection portion of the balloon are a unitary structure.

15. The balloon catheter according to claim 14, further comprising an outer tube possessing a distal portion connected to a proximal portion of the balloon, the elongated shaft being positioned in the outer tube; and the distal portion of the elongated shaft being connected to a distal portion of the balloon.

16. The balloon catheter according to claim 15, wherein the outer tube is spaced apart from the elongated shaft, a filling lumen being located between an inner surface of the outer tube and an outer surface of the elongated shaft, the filling lumen communicating with an interior of the balloon being outwardly expandable when fluid is introduced into the interior of the balloon by way of the filling lumen.

17. The balloon catheter according to claim 16, wherein the elongated shaft comprises a guide wire lumen; and the elongated shaft possesses an open distal-most end.

18. The balloon catheter according to claim 14, wherein the balloon possesses a distal side tapered portion on a distal side of the effective expansion portion, the distal tapered portion possessing an outer diameter which gradually decreases toward the distal side, and wherein the projection portion extends along the distal side tapered portion.

19. The balloon catheter according to claim 14, wherein the projection portion possesses a maximum width that is greater than a base width, the base width being at a location where the projection portion extends radially outward from the outer surface of the balloon.

20. The balloon catheter according to claim 19, wherein the projection portion comprises a first part and a second part of the balloon so that the inner surface of the first part of the balloon faces the inner surface of the second part of the balloon, the first and second parts of the balloon projecting radially outwardly away from parts of the balloon immediately adjacent the first and second parts; and the projection portion includes a gap between the inner surface of the first part and the inner surface of the second part.

* * * * *